(12) United States Patent
Beilfuss et al.

(10) Patent No.: US 8,877,983 B2
(45) Date of Patent: Nov. 4, 2014

(54) PROCESS FOR THE PREPARATION OF 1-ALKYL GLYCEROL ETHERS

(75) Inventors: Wolfgang Beilfuss, Hamburg (DE); Martin Balthasar, Hamburg (DE); Ralf Gradtke, Tornesch (DE); Klaus Weber, Hamburg (DE); Heinz-Georg Steffen, Brinjahe (DE)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 871 days.

(21) Appl. No.: 12/830,552

(22) Filed: Jul. 6, 2010

(65) Prior Publication Data

US 2011/0009676 A1    Jan. 13, 2011

(30) Foreign Application Priority Data

Jul. 8, 2009    (DE) .......................... 10 2009 032 235

(51) Int. Cl.
  *C07C 41/02*  (2006.01)
  *C07C 43/10*  (2006.01)
  *C07C 41/26*  (2006.01)
  *C07C 67/26*  (2006.01)

(52) U.S. Cl.
  CPC ................ *C07C 41/26* (2013.01); *C07C 67/26* (2013.01)
  USPC .......................................... 568/680; 568/580

(58) Field of Classification Search
  CPC ................ C07C 41/26; C07C 67/26
  USPC .................................. 568/680, 580
  See application file for complete search history.

(56) References Cited

FOREIGN PATENT DOCUMENTS

| JP | 58-134049 | * | 8/1983 | ............ C07C 69/003 |
|---|---|---|---|---|
| JP | 58-134049 A | | 8/1983 | |
| JP | 58134049 A | | 8/1983 | |
| JP | 6-25053 A | | 2/1994 | |
| JP | 06025053 | | 2/1994 | |
| JP | 2002-114727 A | | 4/2002 | |

OTHER PUBLICATIONS

DE Office Action dated Mar. 24, 2010 in corresponding 10 2009 032 235.3-43 Dated Mar. 3, 2010.

* cited by examiner

Primary Examiner — Rosalynd Keys
(74) Attorney, Agent, or Firm — Young & Thompson

(57) ABSTRACT

A process for the preparation of a 1-alkyl glycerol ether of the formula (I)

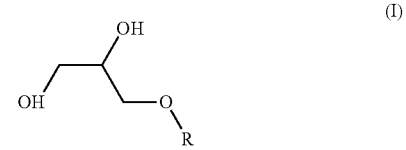

in which: (a) an alkyl glycidyl ether of the formula (II)

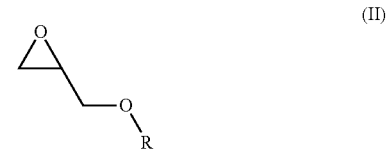

in which R is an unbranched or branched $C_1$- to $C_{24}$-alkyl group, where the alkyl group may be substituted with one or more hydroxy and/or $C_1$- to $C_4$-alkoxy group(s) and/or the alkyl chain may be interrupted by up to four oxygen atoms, is added to: (x) a carboxylic acid having 1-10 carbon atoms; (y) an ester of a carboxylic acid having 1-10 carbon atoms; and/or (z) an anhydride of a carboxylic acid having 1-10 carbon atoms. The low-water reaction mixture containing a catalytic amount of a strong acid is reacted at a temperature of more than 40° C. to give an acylated alkyl glycerol ether; and (b) the acylated alkyl glycerol ether is reacted in order to obtain the alkyl glycerol ether of the formula (I).

10 Claims, No Drawings

PROCESS FOR THE PREPARATION OF 1-ALKYL GLYCEROL ETHERS

The present invention relates to a process for the preparation of 1-alkyl glycerol ethers of high quality for use in cosmetic, pharmaceutical and household products. In particular, the invention relates to a process for the preparation of 1-(2-ethylhexyl)glycerol ether.

The specific alkyl glycerol ether 1-(2-ethylhexyl)glycerol ether (ethylhexylglycerol, old name octoxyglycerol) is a multifunctional additive for cosmetic preparations and, under the registered trade name Sensiva® SC 50 (Schülke & Mayr GmbH, Norderstedt, Federal Republic of Germany), is primarily used as deodorant active ingredient, skincare additive and effect enhancer for selected microbicidal active ingredients.

According to the prior art, ethylhexylglycerol is obtained from 2-ethylhexyl glycidyl ether by Lewis-acid-catalysed reaction with a lower alkanone (e.g. acetone) to give 2,2-dialkyl-4-(2-ethylhexyloxy-methyl)dioxolane and subsequent acidic hydrolysis (e.g. with sulphuric acid) and fractional distillation. This process forms the basis of the industrial synthesis of ethylhexylglycerol. The process inevitably proceeds in more than one stage, is technically complex, susceptible to disturbances (for example in the case of differing starting grades of the starting materials used) and often leads to an unpleasant odour of the product, which then in turn must be purified, which is complex.

Further processes known in the prior art for the preparation of alkyl glycerol ethers are:
1. The reaction of glycerol with alkyl halide in the presence of a base,
2. the reaction of an alcohol with glycerol in the presence of an acidic catalyst and
3. the reaction of an alcohol with glycidol using an acidic or basic catalyst.

These processes have numerous disadvantages:
the preparation does not proceed in a selective manner,
undesired by-products are formed which adversely affect yield, colour and odour and which have unacceptable toxicological effects; these by-products have to be separated off by distillation, which is complex,
handling the starting materials involves risks, e.g. glycidol (2,3-epoxypropanol-1) has a considerable local irritative effect on skin and respiratory tracts, causes severe eye damage, and, in the case of frequent contact, dermatitis and allergic symptoms are possible,
a high salt content is produced,
large amounts of waste products are produced which are not able to be utilized and accordingly have to be disposed of, which is expensive,
the quality of the end product is inadequate for a cosmetic or pharmaceutical application and
sometimes expensive plants and high maintenance expenditure are required (e.g. in the case of pressurized reactions).

According to JP 60 250 53, to prepare alkyl glycerol ethers, in a first stage, acetic acid is added to glycidyl ether and water. The resulting intermediate is then worked-up in a second stage in order to obtain the end product. Here, in the first stage, preferably 5 to 7 mol of water are used, based on the quantitative amount of glycidyl ether. The presence of water leads to a relatively long reaction time and to a low space-time yield. The use of less than 3 mol of water per mole of glycidyl compound leads, according to the disclosure in JP 60 250 53, to the formation of high-boiling by-products and to a low yield of desired alkyl glycerol ether.

According to JP 58 1 340 49, in a first stage, a glycidyl ether is reacted with an acid anhydride in the presence of an acid, such as for example a Lewis acid, preferably at 20 to 40° C. A diacylated glycerol ether is formed. This is then hydrolysed. In the first stage, strict temperature control is necessary. Moreover, the anhydride has to be used in excess, which is not economical.

According to JP 2002 114 727, to prepare a glycerol ether, a mixture of carboxylic acid, base and water is initially introduced, glycidyl ether is added and the epoxide group is opened. In this process, preferably 10 mol of water are used per mole of glycidyl ether, for which reason this process too has a low reaction rate and a low space-time yield.

There is therefore a need for an improved process for the preparation of 1-alkyl glycerol ethers such as ethylhexylglycerol, which does not have the disadvantages of the prior art, is more economical and in particular produces a high-quality product.

Surprisingly, it has now been found that 1-alkyl glycerol ether can be prepared on an industrial scale by a process which offers significant advantages over the prior art.

In a first stage (a) of the process according to the invention, alkyl glycidyl ethers are reacted with lower carboxylic acids, their esters or anhydrides with ring opening to give acyl alkyl glycerol ether derivatives. In a second stage (b), the acyl groups are cleaved off.

Consequently, the present invention relates to a process for the preparation of a 1-alkyl glycerol ether of the formula (I)

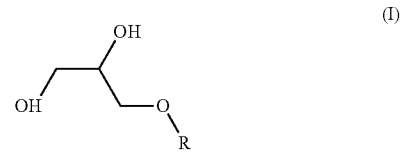

in which
(a) an alkyl glycidyl ether of the formula (II)

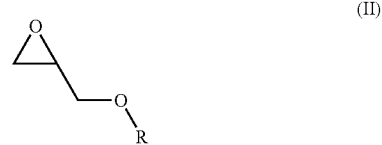

in which R is an unbranched or branched $C_1$- to $C_{24}$-alkyl group, where the alkyl group may be substituted with one or more hydroxy and/or $C_1$- to $C_4$-alkoxy group(s) and/or the alkyl chain may be interrupted by up to four oxygen atoms,
is added to
(x) a carboxylic acid having 1 to 10 carbon atoms,
(y) an ester of a carboxylic acid having 1 to 10 carbon atoms and/or
(z) an anhydride of a carboxylic acid having 1 to 10 carbon atoms
and the low-water reaction mixture containing a catalytic amount of a strong acid is reacted at a temperature of more than 40° C. to give an acylated alkyl glycerol ether, and
(b) the acylated alkyl glycerol ether is reacted in order to obtain the alkyl glycerol ether of the formula (I).

Preferably, the process according to the invention is carried out under inert gas, such as e.g. in a nitrogen atmosphere.

In one possible embodiment, according to the invention, a non-optimally pure 1-alkyl glycerol ether, e.g. from a prior production, can be added to stage (a) and/or stage (b) and thus passed to a work-up.

Preferably, in stages (a) and (b) (and in particular during the preparation of 1-(2-ethylhexyl)glycerol ether), no additional solvents are used. During the preparation of e.g. solid glycerol ethers or when using solid or viscous glycidyl ethers, it is possible to add an inert solvent.

Stage (a)

In stage (a), the glycidyl ether of the formula

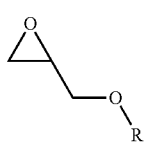

(II)

is acylated. R is preferably a $C_3$- to $C_{18}$-alkyl group, more preferably a $C_6$- to $C_{12}$-alkyl group, most preferably a $C_8$-alkyl group, in particular a 2-ethylhexyl group. Further alternative examples of R are e.g. propyl, hexyl, heptyl, octyl, nonyl, decyl, dodecyl, menthyl, octadecyl, hexadecyl and 9-octadecenyl. According to the invention, it is also possible to use mixtures of the specified glycidyl ethers.

In one preferred embodiment, the carboxylic acid (x) used for the acylation has 1 to 6 carbon atoms, preferably 1 to 3 carbon atoms, most preferably 1 to 2 carbon atoms. The carboxylic acid may be a monocarboxylic acid, in particular formic acid or acetic acid, a dicarboxylic acid, in particular succinic acid or glutaric acid, or a hydroxycarboxylic acid, in particular glycolic acid or lactic acid. The carboxylic acid ester (y) may be a formate or an acetate (e.g. an ester which is distilled off in stage (b)). The carboxylic anhydride (z) may be acetic anhydride or succinic anhydride. It is also possible to use mixed anhydrides, i.e. anhydrides of two different carboxylic acids. It is known to the person skilled in the art that formic anhydride is unknown, but the mixed anhydride of formic acid and acetic acid does exist. In addition, it is possible to use mixtures of (x) carboxylic acid(s), (y) ester(s) and/or (z) anhydride(s).

It is preferred that the molar ratio of alkyl glycidyl ether of the formula (II) to (x) the carboxylic acid, (y) the ester and/or (z) the anhydride is in the range from 1:0.5 to 1:10, preferably from 1:1 to 1:3. It is particularly preferred that the molar ratio is about 1:2.

It is clear to the person skilled in the art that when using an anhydride, primarily diacylated glycerol ethers are obtained, whereas when using the carboxylic acid or the ester, primarily monoacylated glycerol ethers are formed.

The strong acids used in stage (a) have a $pK_a$ value of <4, preferably <3. For the purposes of the description of the present invention, carboxylic acids with a $pK_a$ value <4 (such as formic acid, $pK_a$ value=3.75) are considered to be carboxylic acids (x) and not strong acids. This means that, according to the invention, the presence of a strong acid is prescribed which is not a carboxylic acid.

The strong acid used in stage (a) can be a very strong inorganic acid, in particular sulphuric acid or hydrochloric acid, an organic acid, in particular an alkylsulphonic acid or an arylsulphonic acid, or a solid or polymeric acid, in particular an acidic cation exchanger. Preference is given to using low-water strong acids, such as 96% strength sulphuric acid. It is also possible to use mixtures of strong acids. Preferably, stage (a) takes place in the absence of halogenated acids such as hydrochloric acid, since in their presence the formation of undesired (additional) organohalogen compounds cannot be ruled out.

The molar ratio of alkyl glycidyl ether:carboxylic acid is preferably in the range 1:0.5 to 1:10, preferably 1:1 to 1:3, particularly preferably about 1:2, alternatively particularly preferably about 1:1.

According to the invention, it is preferred that the strong acid and the carboxylic acid are initially introduced and then the glycidyl ether is added. In this embodiment, the fraction of the strong acid in the reaction mixture can be 0.01 to 10% by weight, preferably 0.5 to 5% by weight, particularly preferably 1 to 3% by weight, based on the mixture of carboxylic acid component and strong acid.

Alternatively, the procedure may involve mixing the strong acid and the glycidyl ether and adding it to the carboxylic acid. However, experiments in which the glycidyl ether and the sulphuric acid were initially introduced led to higher fractions of di- and polymers. Moreover, the yield was considerably lower (50% in the crude product), and ultimately it is not favourable to heat the glycidyl ether with, for example, concentrated sulphuric acid.

The process according to the invention is characterized by a lack of water in stage (a). Preferably, the reaction mixture in stage (a) comprises less than 1 mol of water per mole of used alkyl glycidyl ether of the formula (II), such as at most 0.9 mol, more preferably at most 0.7 mol, most preferably at most 0.5 mol, of water, based on the quantitative amount of used alkyl glycidyl ether of the formula (II).

Expressed in another way, the water content in stage (a) is preferably less than 20% by weight, more preferably less than 10% by weight, in particular less than 5% by weight, such as, for example, less than 4% by weight, less than 3% by weight, less than 2% by weight or in particular less than 1% by weight, based on the reaction mixture (comprising glycidyl ether of the formula (II) plus (x), (y) and/or (z) and optionally water).

The reaction of 2-ethylhexyl glycidyl ether with formic acid in the molar ratio 1:2 produced, when using pure formic acid (purity >99% by weight), a high-quality product in high yield. When using aqueous formic acid (85% by weight), the yield was comparable with the reaction of "pure" formic acid, although the odour of the end product was somewhat worse, but entirely usable in e.g. industrial applications. When using formic acid with a content of 50% by weight (corresponding to a water content of 25% by weight or 5.1 mol of water per mole of glycidyl ether), yield and odour were no longer acceptable. The reaction with formic acid with a content >80% by weight, preferably >85% by weight, in particular >90% by weight or >95% by weight, such as >98% by weight, or >99% by weight as carboxylic acid component (x) thus gives a better odour of the end product than with dilute formic acid and is consequently preferred.

The reaction in stage (a) takes place preferably at a temperature in the range from 55 to 110° C., more preferably 60 to 105° C., in particular at about 65° C.

Preferably, in the process according to the invention, in stage (a), the process involves initially introducing the carboxylic acid, the ester of the carboxylic acid and/or the anhydride of the carboxylic acid, adding the strong acid, and heating the mixture of carboxylic acid and strong acid to 50 to 120° C., preferably to 55 to 110° C., most preferably to 60 to 105° C., in particular to about 65° C. The alkyl glycidyl ether of the formula (II) is then added, preferably in portions and in particular dropwise. During the addition, stirring is carried out if necessary, where the temperature of the mixture is preferably at least 45° C., in particular at least 50° C., and/or preferably does not exceed 150° C., more preferably 120° C., most preferably 100° C.

The reaction temperature is, for example, about 65° C.: formic acid is initially introduced, sulphuric acid is added, the mixture is heated to 65° C. and, with stirring at 65° C., the glycidyl ether is added, where, with cooling, the addition is controlled such that a reaction temperature of 70° C. is not exceeded. The reaction is held at the lowest possible temperature in order to avoid possible decomposition of the formic acid to CO and water.

In stage (a), water-binding agents can be added, for example calcium chloride, sodium sulphate or magnesium sulphate, and water-binding porous particles such as e.g. molecular sieve. Since the carboxylic acid anhydrides (y) and carboxylic acid esters (z) possible as reactant bind water, in the case of their use, the specified water-binding agents are preferably not added.

Stage (b)

In stage (b), the acylated glycerol ether is reacted in order to obtain the 1-alkyl glycerol ether of the formula (I). Here, it is possible that, in stage (a), the acylated glycerol ether is worked up and this is then used in stage (b). However, it is preferred that, in stage (b), the product from stage (a) is used without working up the acylated glycerol ether.

In one preferred embodiment of stage (b), which is referred to hereinbelow as (b)(i), the reaction takes place by virtue of the fact that the acylated alkyl glycerol ether is hydrolysed with alkalizing agent at a pH>7 and is then neutralized and fractionally distilled in order to obtain the 1-alkyl glycerol ether of the formula (I). Isolation of the 1-alkyl glycerol ether takes place by fractional distillation. The reaction procedure in stage (b)(i) preferably takes place by hydrolysing the acylated alkyl glycerol ether with aqueous alkali metal hydroxide at a temperature in the range from 20° C. to 80° C.

In embodiment (b)(i), the hydrolysis of the acylated glycerol ether with aqueous alkali metal hydroxide can take place (e.g. at room temperature or higher temperature such as e.g. 40° C. or 80° C.). However, stage (b) of the process (and in particular the transesterification of the acylated glycerol ether with alcohol to carboxylic acid ester according to (b)(ii)) also preferably takes place under low-water conditions, as explained below.

In one alternatively preferred embodiment of stage (b), which is referred to hereinbelow as (b)(ii), the (preferably acid-catalysed) reaction takes place by transesterifying by adding an excess molar amount of aliphatic alcohol having 1 to 4 carbon atoms, and distilling off the resulting alkyl ester of the carboxylic acid and of the aliphatic alcohol and the excess of aliphatic alcohol. In one preferred embodiment, the acylated glycerol ether is present in the reaction vessel and the alcohol is added, which has the advantage that the reaction product remains as obtained in the reaction vessel. Then, the catalytic amount of strong acid remaining in the reaction solution is neutralized with alkalizing agent, and then the mixture is fractionally distilled in order to obtain the alkyl glycerol ether of the formula (I).

Embodiment (b)(ii) of the process according to the invention is preferred over embodiment (b)(i).

In stage (b)(ii), preference is given to working under low-water conditions. The water content in stage (b) is preferably less than 20% by weight, more preferably less than 10% by weight, in particular less than 5% by weight, such as, for example, less than 4% by weight, less than 3% by weight, less than 2% by weight or in particular less than 1% by weight, based on the reaction mixture.

In stage (b)(ii), the aliphatic alcohol used may be, for example, ethanol or methanol. Here, methanol is preferred. It is also possible to use mixtures of aliphatic alcohols.

The reaction procedure in stage (b)(ii) can take place such that, prior to the transesterification, the mixture is cooled to a temperature below the boiling temperature of the aliphatic alcohol (alternatively below the boiling temperature of the ester which forms). Here, the procedure typically involves, following the addition of the total amount of the glycidyl ether in stage (a), at the end of the reaction, afterstirring for a certain time, such as e.g. 1 hour, at the optimum reaction temperature. Only then is the reaction mixture cooled (e.g. by air cooling or water cooling) to a temperature below the boiling temperature of the alcohol used for the transesterification (or of the ester which forms), so that the plant in stage (b)(ii) can be operated safely.

During a distillative separation, in the case of a 1-pot process, the following should be noted: following the reaction of the glycidyl ether with, for example, the carboxylic acid (x) (=stage (a)), alcohol is added to the acylated glycerol ether (=stage (b)(ii)). The ester of carboxylic acid and alcohol is removed from the equilibrium by distillation. If the transesterification has finished and if the ester of carboxylic acid and alcohol has been distilled off quantitatively, the remaining alcohol is removed by distillation. The catalytic amount of strong acid is then neutralized. Now, the 1-alkyl glycerol ether can be distilled (for example in vacuo). In order to be able to carry out the separation usefully, the ester of carboxylic acid and alcohol should have a boiling point which is significantly below the boiling points of the other components. This ensures that this ester can be removed from the equilibrium, i.e. the transesterification takes place.

The following overview lists examples of boiling temperature differences between alcohol and ester:

| Carboxylic acid (x) | Alcohol | Ester | Δ [K][1] |
|---|---|---|---|
| Formic acid | Methanol | Methyl formate | 32 |
| Formic acid | Ethanol | Ethyl formate | 25 |

[1]Boiling temperature difference (b.p.$_{alcohol}$ − b.p.$_{ester}$)

For a boiling temperature difference Δ>20 K, quantitative removal of the ester by distillation from the equilibrium in this process is economically particularly simple. The above table shows that, as carboxylic acid (x) in stage (a), particularly preferably formic acid is most suitable and, as alcohol in stage (b)(ii) methanol is best suited. Ethanol as alcohol in stage (b)(ii) is one alternative despite higher costs, a larger molar volume and thus lower yield for the same batch size etc. on account of its lower toxicity.

In one particularly preferred embodiment (which is referred to hereinbelow as 1-pot process), the transesterification (b)(ii) takes place in the same reaction container in which the reaction (a) has taken place. Here, in stage (b)—after distilling off the low-boiling components, the crude product is neutralized with alkalizing agent, such as NaOH, and subjected to a fractional distillation in vacuo. Preferably, in stage (a), no Lewis acids are used as strong acids since they can lead to undesired by-products, especially in the case of the described 1-pot process.

Irrespective of whether the procedure in stage (b) is in accordance with (i) or (ii), it is preferred that, after the fractional distillation in stage (b)(i) or (b)(ii), a stabilizer is added to the 1-alkyl glycerol ether of the formula (I).

The alkalizing agent in stage (b)(i) or (b)(ii) may be, for example, an alkali metal hydroxide such as sodium hydroxide or potassium hydroxide, an alkaline earth metal oxide or hydroxide such as calcium hydroxide or calcium oxide and/or an alkali metal or alkaline earth metal carbonate or hydrogencarbonate. Preference is given to using a concentrated aqueous solution of sodium hydroxide and/or potassium hydroxide.

It is assumed that the organohalogen (AOX) content in the product in the 1-pot process according to the invention is reduced as a result of the distillation of an inevitably salt-containing (strong acid from the neutralization+alkalizing agent) crude product. If required, the salt content can be increased and/or it is possible to add organohalogen-reducing additives (e.g. alkali metal carbonate, alkali metal hydrogencarbonate).

Preferred alkyl glycidyl ethers have a content of at least 80% by weight, more preferably of at least 90% by weight, particularly preferably of at least 99% by weight.

Following the current industrial production process, the resulting product may be contaminated with organic chlorine compounds which originate from the starting material (glycidyl ether, prepared from epichlorohydrin and 2-ethylhexyl alcohol) and are difficult to remove by distillation. In this known process, the end product at no point comes into contact with an alkaline reaction medium which would lead to a degradation of the organohalogen compounds. By contrast, the invention is based inter alia on the fact that the process according to the invention preferably includes the treatment with an alkalizing agent (e.g. for neutralization of the catalyst acid). Here, the treatment with the alkalizing agent is carried out such that (optional variation in the amount, temperature, treatment time) degradation of organohalogen compound takes place in a targeted manner without losses in yield and quality of the end product.

The process according to the invention offers the following advantages:
- economical,
- high yield,
- high selectivity,
- 1-pot process possible, i.e. no intermediates have to be isolated, stored or handled in any other way,
- high quality of the end product (in particular as regards colour, odour, stability, impurities),
- type and amount of the impurities are significantly reduced (e.g. glycidyl ether, 2-ethylhexanol, organohalogen compounds), in particular 1,3-bis(2-ethylhexyloxy)propan-2-ol, that is difficult to separate off by distillation, is formed in a barely detectable amount during the described reaction,
- low potential for disruption of the process (e.g. as a result of quality fluctuations in the starting materials),
- low expenditure when acquiring and storing the starting materials, providing and maintaining the plants, preparing and cleaning the plants, disposing of the residues,
- a low-organohalogen, preferably organohalogen-free, product is obtained,
- no use (and disposal) of additional solvents, including water,
- comparatively few and small amounts of nonutilizable waste products are produced,
- economic utilization of reaction products (e.g. carboxylic acid esters) possible,
- reutilization of reactants following separation possible (e.g. lower alcohols, possibly contaminated by carboxylic acid ester; e.g. reuse of carboxylic acid ester from stage (b) in stage (a)),
- comparatively gentle reaction conditions
- compact reaction volume (comparatively low reaction volume for high yield, e.g. ca. 875 g starting materials produce 320 g of end product in the 1-pot process),
- high space/time yield,
- high plant capacity utilization possible, and
- comparatively short reaction times.

The advantages of the invention are evident in particular from the following examples. The investigations show that the reaction with 100% strength formic acid produces a better odour of the end product than with dilute formic acid.

EXAMPLES 4 mol of formic acid (98% strength, BASF) and 2 g of concentrated sulphuric acid were heated to 80° C. and admixed with a total of 2 mol of 2-ethylhexyl glycidyl ether in such a way that the reaction temperature of 100° C. was not exceeded. The mixture was then stirred for a further hour at 95° C., then cooled to 60° C., admixed with a molar excess (9 mol) of methanol and the methyl formate was distilled off via a column. The residue was neutralized with NaOH and distilled in vacuo. This gives clear, colourless, low-odour product (2-ethylhexyl glycerol ether) in 78.1% yield. The product has a purity of 99.5%.

In a further experiment according to the invention, transesterification was carried out in stage (b) with ethanol. The yield was 65.7%. In a corresponding comparative experiment (in stage (a) without sulphuric acid) in which transesterification was carried out in stage (b) likewise with ethanol, the yield was just 56.7%.

The invention claimed is:
1. A process for the preparation of a 1-alkyl glycerol ether of the formula (I)

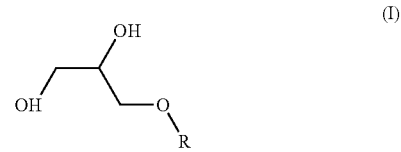

in a high yield with reduced impurities, comprising the stages of:
(a) obtaining an acylated alkyl glycerol ether by reacting, at a temperature of more than 40° C., a reaction mixture comprising:
(i) an alkyl glycidyl ether of the formula (II)

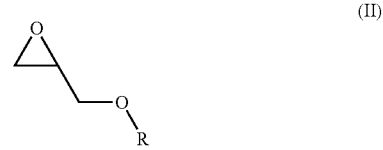

in which R is an unbranched or branched $C_1$- to $C_{24}$-alkyl group, where the alkyl group may be substituted with one or more hydroxy and/or $C_1$- to $C_4$-alkoxy group(s) and/or the alkyl chain may be interrupted by up to four oxygen atoms,
(ii) a carboxylic acid having 1 to 10 carbon atoms,
(iii) a catalytic amount of a strong acid having a pKa value of less than 4, said strong acid not being a carboxylic acid, and (iv) at most 0.7 mol of water per mole of alkyl glycidyl ether of the formula (II), said alkyl glycidyl ether of the formula (II) and said a carboxylic acid present in a molar ratio of 1:0.5 to 1:10; and (b) transesterifying the acylated alkyl glycerol ether obtained from stage (a) by adding an excess molar amount of aliphatic alcohol having 1 to 4 carbon atoms to form a reaction product, distilling off an alkyl ester of the carboxylic acid and of the aliphatic alcohol and excess aliphatic alcohol formed from the transesterifying, neutralizing the strong acid remaining with the reaction product with alkalizing agent, and fractionally distilling in order to obtain the alkyl glycerol ether of the formula (I).

2. The process according to claim 1, wherein R is a $C_3$ to $C_{18}$ alkyl group.

3. The process according to claim 1, wherein the carboxylic acid has 1 to 6 carbon atoms.

4. The process according to claim 1, wherein the carboxylic acid is a monocarboxylic acid, a dicarboxylic acid, or a hydroxycarboxylic acid.

5. The process according to claim 1, wherein the strong acid is an inorganic acid, an organic acid, or a solid or polymeric acid.

6. The process according to claim 1, wherein to form the reaction mixture of stage (a), the carboxylic acid is initially introduced, the strong acid is added, the mixture is heated to 50 to 120° C., then the alkyl glycidyl ether of the formula (II) is added in portions, and optionally with stirring, where the temperature of the mixture is at least 45° C.

7. The process according to claim 1, wherein, the reaction mixture of stage (a) further comprises water-binding agents.

8. The process according to claim 1, wherein the alkalizing agent in stage (b) is an alkali metal hydroxide, an alkaline earth metal hydroxide, and/or an alkali metal or an alkaline earth metal carbonate or hydrogencarbonate.

9. The process according to claim 1, wherein, prior to the transesterification in stage (b), the mixture is cooled to a temperature below the boiling temperature of the aliphatic alcohol.

10. The process according to claim 1, wherein, after the fractional distillation in stage (b), a stabilizer is added to the 1-alkyl glycerol ether of the formula (I).

\* \* \* \* \*